United States Patent [19]

Kakizawa

[11] Patent Number: 4,801,249
[45] Date of Patent: Jan. 31, 1989

[54] SMALL-SIZED PUMP

[75] Inventor: Goro Kakizawa, Tokyo, Japan

[73] Assignee: Ohken Seiko Co., Ltd., Japan

[21] Appl. No.: 57,780

[22] Filed: Jun. 3, 1987

[30] Foreign Application Priority Data

Jun. 9, 1986 [JP] Japan ................................. 61-133435
Oct. 22, 1986 [JP] Japan ........................... 61-161678[U]

[51] Int. Cl.$^4$ ........................ F04B 1/28; F04B 39/10
[52] U.S. Cl. ................................. 417/269; 417/566;
92/98 D; 92/48
[58] Field of Search .............. 417/479, 473, 269, 271,
417/566; 92/48, 98 D

[56] References Cited

U.S. PATENT DOCUMENTS

| | | | |
|---|---|---|---|
| 1,715,735 | 6/1929 | Banning, Jr. | 417/473 |
| 2,457,339 | 12/1948 | Bertea | 417/269 |
| 2,991,723 | 7/1961 | Zubaty | 92/48 |
| 3,029,742 | 4/1962 | Curtis | 417/479 |
| 3,987,938 | 10/1976 | Cooprider | 417/479 |
| 4,090,818 | 3/1978 | Hope | 417/473 |
| 4,115,042 | 9/1978 | Schroeder | 417/479 |
| 4,486,151 | 12/1984 | Wesala | 417/566 |
| 4,507,058 | 3/1985 | Schoenmeyer | 417/271 |
| 4,570,833 | 2/1986 | Vanderjagt | 417/269 |
| 4,610,605 | 9/1986 | Hartley | 417/269 |

FOREIGN PATENT DOCUMENTS

| | | | |
|---|---|---|---|
| 476099 | 8/1951 | Canada | 417/269 |
| 48307 | 7/1983 | Japan | 417/479 |

Primary Examiner—William L. Freeh
Attorney, Agent, or Firm—Irell & Manella

[57] ABSTRACT

A small-sized pump comprising a common valve chamber, a plural number of pump chambers respectively arranged round the common valve chamber and each having a diaphragm, a drive member provided in the inclined state and serving to move the diaphragms upward and downward, and a tubular supporting member extending obliquely downward from the central portion of the drive member, the small-sized pump being arranged to make the end of the tubular supporting member perform circular motion and to thereby drive the drive member so as to move the diaphragms upward and downward so that respective pump chambers perform pumping actions with a predetermined time lag, the small-sized pump being thereby arranged to have high pumping efficiency.

14 Claims, 3 Drawing Sheets

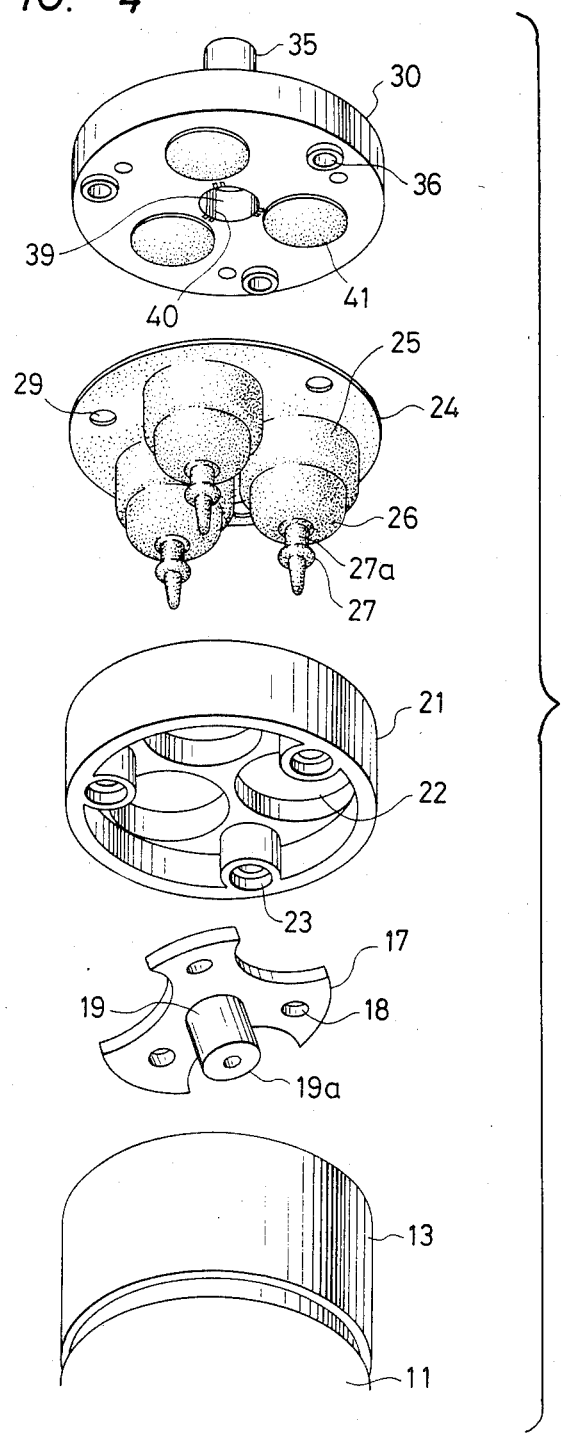

4,801,249

SMALL-SIZED PUMP

BACKGROUND OF THE INVENTION (a) Field of the Invention

The present invention relates to a small-sized pump and, more particularly, to a small-sized pump which makes it easy to assemble the pump and motor into one unit and which is especially suitable for the use with a simplified-type sphygmomanometer and the like.

(b) Description of the Prior Art

In recent years, simplified-type sphygmomanometers by which people in general can measure the blood pressure by themselves are put on the market. The above-mentioned type of sphygmomanometers employ a pump which is driven by a small-sized and powerful pump.

The above-mentioned kind of known pumps are constructed as shown in FIGS. 1 and 2. That is, FIG. 1 shows a side view and FIG. 2 shows a front view of said known pump. In said figures, numeral 1 designates a base, numeral 2 designates a small-sized DC motor, numeral 3 designates an output shaft of the motor 2, numeral 4 designates an eccentric cam which is fixed to the output shaft 3, numeral 5 designates a drive shaft which is fixed to the eccentric cam in a position eccentric from the output shaft 3, numeral 6 designates a bearing which is slidably fitted to the drive shaft 5, numeral 7 designates a rod which is fixed to the bearing 6, and numeral 8 designates a diaphragm unit which is fixed to the base 1 and which constitutes the pump together with a part of the base 1. The diaphragm unit 8 is constructed as illustrated by the sectional view shown in FIG. 3. That is, a diaphragm 10 is fixed to a case 9, and the central portion of the diaphragm 10 is fixed to the end of the rod 7.

The known small-sized pump constructed as mentioned in the above operates as described below. That is, when the motor 2 is energized and started, the output shaft 3 rotates and, therefore, the drive shaft 5 revolves round the output shaft 3 so as to make the rod 7 move upward and downward. As the rod 7 moves upward and downward as mentioned in the above, the central portion of the diaphragm 10 in the diaphragm 8 performs reciprocating motion in the substantially vertical direction and, consequently, the pumping action is performed.

In case of said known pump, the height of the pump becomes large because a long rod is used and, moreover, the motor and diaphragm unit are arranged at positions distant from each other. Therefore, the pump as a whole becomes large, and it is difficult to make the pump small in size.

If the rod is made short, it becomes difficult to make the diaphragm perform the reciprocating motion. As a result, the diaphragm is deformed forcibly, and the power consumption becomes large.

Moreover, as the diaphragm unit 8 is so constructed that the diaphragm 10 has a comparatively flat shape and the circumferential portion of the diaphragm 10 is fixed to the case 9, the portion 10a of the diaphragm 10 swells as shown by the chain lines in FIG. 3 when the rod comes down and the internal pressure increases and, consequently, it is impossible to obtain sufficient pressure increase.

SUMMARY OF THE INVENTION

It is, therefore, a primary object of the present invention to provide a small-sized pump comprising a common valve chamber having a delivery port, a plural number of pump chambers respectively arranged on a substantially same circular line round said common valve chamber and each having a diaphragm, communicating portions arranged to make said pump chambers respectively communicate with said common valve chamber, a tubular valve body arranged to cover said communicating portions and to form first check valves, suction ports provided to each of said pump chambers, second check valves provided to said suction ports, drive portions respectively provided to said diaphragms constituting said pump chambers, and a source of driving force arranged to drive said drive portions, said small-sized pump being arranged that said diaphragms are respectively driven by said drive portions so that said diaphragms respectively perform reciprocating motions in the axial direction of an output shaft of said source of driving force in the state that a predetermined time lag is maintained between reciprocating motions of said diaphragms, said respective pump chambers being thereby arranged to repeatedly perform pumping actions in turn so that the fluid from respective pump chambers is thereby delivered through said common valve chamber and, then, through said delivery port, said small-sized pump being thereby arranged to have high pumping efficiency.

BRIEF DESCRIPTION OF THE DRAWINGS

FIG. 4 shows an exploded view of a preferred embodiment of the small-sized pump according to the present invention;

DETAILED DESCRIPTION OF THE PREFERRED EMBODIMENT

Now, the small-sized pump according to the present invention is described in detail below based on a preferred embodiment referring to the accompanying drawings.

Figure 5:
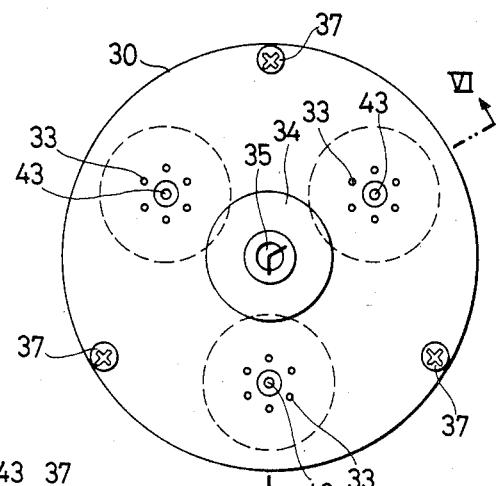
FIG. 5 shows a plan view of said preferred embodiment in the assembled state.
Figure 6:
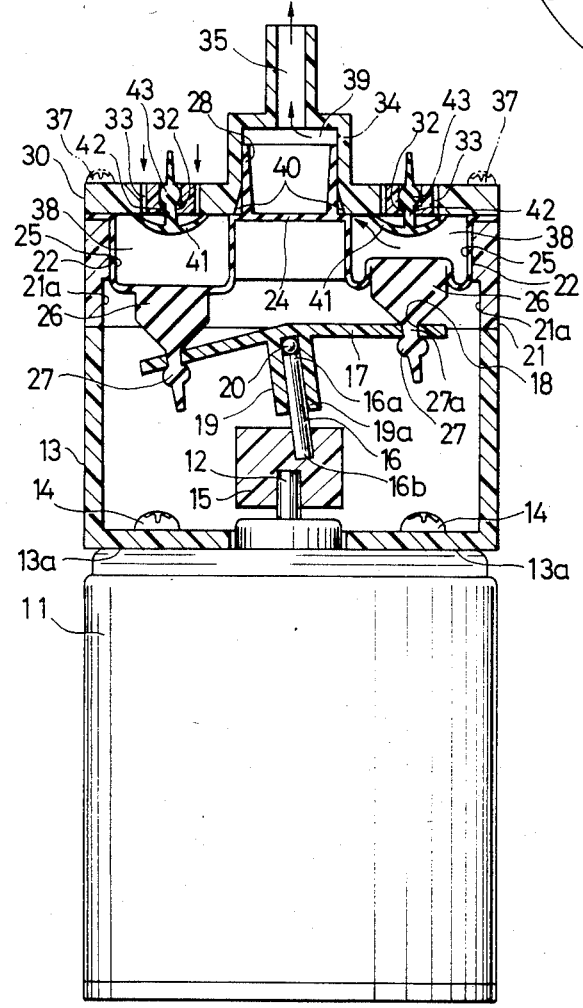
FIG. 6 shows a sectional view taken along the line VI—VI in FIG. 5.

On the accompanying drawings, FIG. 4 shows an exploded view of a preferred embodiment f the small-sized pump according to the present invention, FIG. 5 shows a plan view of said preferred embodiment in the assembled state, and FIG. 6 shows a sectional view taken along the line VI—VI in FIG. 5.

In said figures, numeral 11 designates a source of driving force arranged as a small-sized DC motor, numeral 12 designates an output shaft of the motor 11, numeral 13 designates a first casing with a shape like a cup whose diameter is approximately same as that of the motor 11 and whose bottom surface 13a is fixed to the motor by screws 14, numeral 15 designates a collar fixed to the output shaft 12, numeral 16 designates a drive shaft fixed to the collar 15 in the state that the drive shaft 16 is inclined in respect to the axis of the output shaft 12 and that the end of the drive shaft 16 comes to a position on the extension line of the axis of the output shaft 12, numeral 17 designates a drive member having a shape like a disk and having three fitting holes 18 which are respectively formed at positions of 120° angular distance from each other on a substantially same circular line, and numeral 19 designates a tubular supporting member which extend downward from the central portion of the drive member 17 and which is formed to be integral with the drive member 17. The tubular supporting member 19 is slidably fitted to the drive shaft 16. Numeral 20 designates a steel ball provided in order to reduce the friction between the drive shaft 16 and tubular supporting member 19 of the drive member 17.

Numeral 21 designates a second casing having a shape like a cup and having three cylinder-like portions 22 which are respectively formed at the bottom thereof (said bottom is shown at the top on the drawing) at positions of 120° angular distance from each other on a substantially same circular line. The second casing 21 has three holes 23 for screws which are respectively formed at intermediate positions between respective cylinder-like portions 22.

Numeral 24 designates a diaphragm body made of an elastic material such as soft rubber, soft plastic, etc. and having a shape substantially like a disk, numeral 25 designates three cup-type diaphragm portions which respectively extend downward from the diaphragm body 24 at positions of 120° angular distance from each other on a substantially same circular line and which are formed to be integral with the diaphragm body 24, numeral 26 designated drive portions (pistons) each formed at the central portion at the bottom of each diaphragm portion 25 and formed to be integral with the diaphragm portion 25, numeral 27 designates head portions each formed at the end of each drive portion 26 in the state that a neck portion 27a with a smaller diameter is formed between the drive portion 26 and head portion 27, and numeral 28 designates a tubular valve body which extends upward from the central portion of the diaphragm body 24 and which is formed to be integral with the diaphragm body 24. The drive portions 26 of respective diaphragm portions 25 are connected to the drive member 17 by pushing respective head portions 27 into the corresponding fitting holes 18 of the drive member 17.

Numeral 30 designates a cover member having a shape substantially like a disk and having three valve fitting holes 32 respectively formed at positions of 120° angular distance from each other on a substantially same circular line, numeral 33 designates air suction ports provided round respective valve fitting holes 32, numeral 34 designates a valve casing which extends upward from the central portion of the cover body 30 and which is formed to be integral with the cover body 30, numeral 35 designates an air delivery port provided at the top of the valve casing 34, numeral 36 designates holes for passing the screws therethrough, and numeral 37 designates screws to be passed through the holes 36, 29 and 23 and to be screwed into the tapped holes (not shown on the drawings) provided to the first casing 13. By the screws 37, the cover member 30 is fixed to the second casing 21 by putting the diaphragm body 24 therebetween and is assembled as shown in FIG. 6, and three pump chambers 38 are thereby formed by means of the bottom surface of the cover member 30 and diaphragm portions 25. Besides, a common valve chamber 39 is formed in the valve casing 34 which is formed to be integral with the cover member 30, air passage grooves 40 are provided to the cover member 30 at portions thereof close to the circumferential portion of the valve casing 34, and respective pump chambers 38 are arranged to communicate with the common valve chamber 39 by means of said air passage grooves 40. Furthermore, the tubular valve body 28 is kept in close contact with the inner wall surface of the valve casing 34 and thereby covers the communication passages formed by the air passage grooves 40. Thus, first check valves are formed.

Numeral 41 designates dish-type valve bodies made of an elastic material such as soft rubber or the like, numeral 42 designates supporting pins each extending upward from the central portion of each dish-type valve body 41 and formed to be integral with the valve body 41, and numeral 43 designates head portions each formed at the end of each supporting pin 42. Each dish-type valve body 41 is fixed to the cover member 30 by pushing the head portion 43 into the corresponding valve fitting hole 32 in the state that the valve body 41 covers the air suction ports 33 provided to the cover member 30. Thus, second check valves are formed.

Now, the operation of the preferred embodiment of the small-sized pump according to the present invention constructed as shown in the above is described below.

Figure 1:
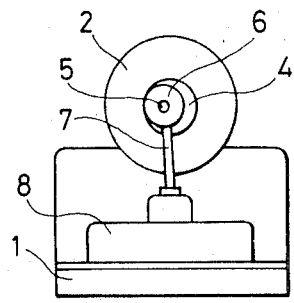
FIG. 1 shows a side view of a known small-sized pump.
Figure 2:
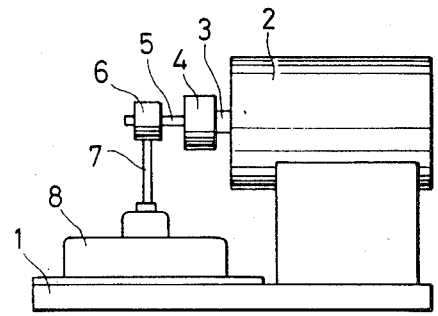
FIG. 2 shows a front view of said known small-sized pump.
Figure 3:
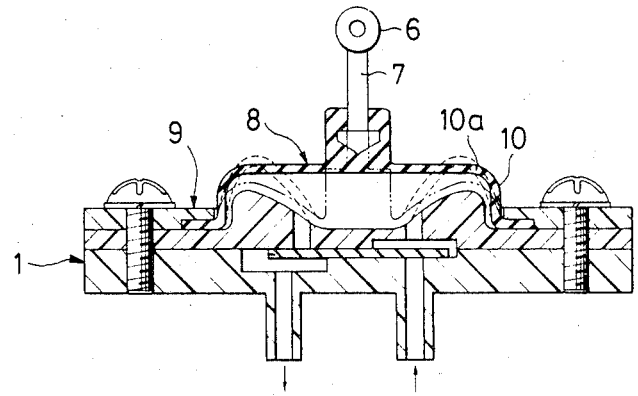
FIG. 3 shows a sectional view of said known small-sized pump.
Figure 7:
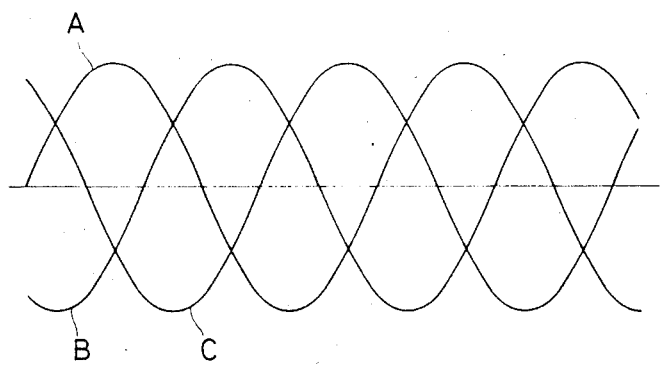
FIG. 7 shows a graph illustrating the upward and downward motions of respective diaphragm portions of said preferred embodiment.

When the motor 11 is energized and the output shaft 12 rotates, the collar 15 also rotates and the drive shaft 16 is thereby moved. At that time, the drive shaft 16 moves in such manner that the upper end 16a thereof functions like a pivot and the lower end 16b thereof performs circular motion round the axis of the output shaft 16. As the drive shaft 16 moves as mentioned in the above, the drive member 17 moves in such manner that the end 19a of the tubular supporting member 19 performs circular motion round the extension line of the axis of the output shaft 16 by using the position of the steel ball 20 as a pivot, and the circumferential portion of the disk-shaped portion of the drive member 17 moves upward and downward. The upward and downward movement of the circumferential portion of the drive member 17 is performed in such manner that individual points thereof move upward and downward with a phase difference corresponding to the difference between there positions in the circumferential direction (difference in the angle). For example, for the three fitting holes 18 provided at the positions for fitting respective diaphragm portions 25 to the drive member 17, the heights thereof vary cyclically, as the time passes, as respectively shown by curves A, B and C in FIG. 7. The phase difference between adjacent ones of those three points (points of the three holes 18) is 120°, which is equal to the angular distance between respective holes 18 (angle between respective holes 18 seen from the center of the disk-shaped portion). In other words, individual points located on a circular line (in the circumferential direction) on the drive member 17 move upward and downward with a positional difference which corresponds to the angular distance between those points.

By the above-mentioned movement of the drive member 17, the drive portions (pistons) 26 of respective diaphragm portions 25 are oscillated upward and downward with a phase difference of 120°. Because of the above-mentioned reciprocating motions (piston-like movements) of respective diaphragm portions 25, respective pump chambers 38 cause cyclical variation in the volume thereof with a phase difference of 120°. In other words, when the drive portion 26 of one of the diaphragm portions 25 moves downward and the volume of the corresponding pump chamber 38 is thereby decreased, the air pressure in that pump chamber 38 decreases, and the tubular valve body 34 comes into close contact with the valve casing 34 and closes the corresponding groove 40 which is the communication passage. On the other hand, the corresponding dish-type valve body 41 opens, and air flows into the pump chamber 38 through the air suction ports 33. When the drive portion 26 moves then upward and the volume of the pump chamber 38 is thereby decreased, the air pressure in that pump chamber 38 rises, and the dish-type valve body 41 comes into close contact with the cover member 30 and close the air suction ports 33. On the other hand, the tubular valve body 28 is opened at the position of the corresponding groove 40 by means of the air pressure, and the air in the pump chamber 38 is delivered through the air delivery port 35 passing through the common valve chamber 39.

By the operation described so far, each pump chamber 38 performs one pumping action during one revolution of the drive shaft 16. Therefore, the pump as a whole performs three pumping actions during one revolution of the drive shaft 16, and the operation efficiency is high.

Besides, the pump according to the present invention is so constructed that the pump means and motor are put into one integral unit and, therefore, it is possible to make the size as a whole very small because the pump chambers are arranged to be integral with the motor, three pump chambers are arranged in the circumferential direction round the common valve chamber provided at the central portion and, moreover, the drive member is arranged between the motor and pump chambers. Furthermore, as the drive member 17 is formed to have a disk-like shape and is arranged that the end of the tubular supporting member 19 thereof performs circular motion so as to thereby make respective pump chambers perform pumping actions with a predetermined phase difference, it is possible to make respective diaphragm portions 25 perform reciprocating motions (piston-like movements) by keeping a predetermined correlation in spite of the fact that the accommodating space is narrow and, therefore, the pumping actions are performed smoothly and efficiently. Moreover, as the cup-type diaphragm portions 25 are inserted to the cylinder-like portions 22, the diaphragm portion 25 does not swell even when the pressure in the pump chamber rises and, therefore, it is possible to rise the pressure satisfactorily.

In the preferred embodiment described so far, three pump chambers are provided. However, the number of pump chambers is not limited to three. That is, when an adequate number of pump chambers are provided on a substantially same circular line round the valve casing 34, it is possible to obtain a high-efficiency small-sized pump in which a large number of pump chambers are arranged in a narrow space. Besides, in the preferred embodiment, the valve body 28 is formed to have an integral tubular shape. However, the valve body 28 may be also formed to have cut portions of a number corresponding to the number of diaphragms to be provided and may be arranged that respective grooves 40 are covered with the portions between those cut portions. As another method, the valve body 28 may be divided into a plural number of valve bodies separate from each other, i.e., of a number corresponding to the number of diaphragms to be provided, and may be arranged that respective grooves 40 are covered with individual valve bodies. For the diaphragm portions 25, it is also possible to form individual diaphragm portions separately from each other and to assemble them together. However, for easier assembly and for other reasons, it is the most preferable to adopt the integrally formed diaphragm portions.

As described so far, the small-sized pump according to the present invention makes it easy to assemble the pump means integrally with the motor and is arranged to be small in size and to have high pumping efficiency and, therefore, it is extremely effective especially when used with a simplified-type sphygmomanometer or the like.

I claim:

1. A diaphragm pump comprising a common valve chamber having a delivery port, a casing having a plural number of cylinders respectively arranged on a substantially same circular line round said common valve chamber, diaphragms respectively arranged in said cylinders and having end portions, to form pump chamber communication portions arranged to make said pump chambers respectively communicate with said common valve chamber, first check valves respectively arranged in said communicating portions, suction ports provided to each of said pump chambers, second check valves provided to said suction ports, drive portions respectively provided to said diaphragms constituting said pump chambers, and a source of driving force arranged to drive said drive portions, said diaphragms being in a cup-like form having outer circumferences arranged in contact with the inside wall surfaces of said cylinders at portions spaced from the end portions thereof, said diaphragm pump being arranged that said diaphragms are respectively driven by said drive portions so that said diaphragms respectively perform reciprocating motions in the axial direction of an output shaft of said source of driving force in such a manner that a predetermined time lag is maintained between said reciprocating motions of said diaphragms, and said diaphragm pump being arranged that said respective pump chambers are thereby made to repeatedly perform pumping action in turn so that the fluid from said respective pump chambers is delivered through said delivery port after passing through said common valve chamber.

2. A diaphragm pump according to claim 1 further comprising a drive member and a tubular supporting member wherein said drive member is arranged that the center thereof is located on the axis of said output shaft of said source of driving force and said drive member is inclined in respect to said axis of said output shaft and that said drive portions of said diaphragms are respectively fixed thereto at positions near the circumferential portion of said drive member, and wherein said tubular supporting member is arranged to extend from the central portion of said drive member in the direction perpendicular to said drive member, said small-size pump being arranged that said drive member is driven by said source of driving force in such manner that the end of said tubular supporting member performs circular motion round said axis of said output shaft of said source of driving force so as to thereby make said respective pump chambers perform pumping actions.

3. A small-sized pump according to claim 1 further comprising a drive member and a tubular supporting member wherein said drive member is arranged that the center thereof is located on the axis of said output shaft of said source of driving force and said drive member is inclined in respect to said axis of said output shaft and that said drive portions of said diaphragms are respectively fixed thereto at positions near the circumferential portion of said drive member, and wherein said tubular supporting member is arranged to extend from the central portion of said drive member in the direction perpendicular to said drive member, said small-sized pump being arranged that said drive member is driven by said source of driving force in such manner that the end of said tubular supporting member performs circular motion round said axis of said output shaft of said source of driving force so as to thereby make said respective pump chambers perform pumping actions.

4. A small-sized pump according to claim 3 further comprising a collar fixed to said output shaft of said source of driving force, and a drive shaft arranged that one end thereof is eccentrically fixed to said collar in the state that said drive shaft is inclined and the other end thereof is slidably fitted into said tubular supporting member, said small-sized pump being arranged that said drive member is driven through said drive shaft and said tubular supporting member by means of rotation of said collar to be given by the driving force from said source of driving force.

5. A small-sized pump according to claim 1 wherein said tubular valve body forming said first check valves is arranged to have cut portions provided at portions other than those portions corresponding to said communicating portions.

6. A small-sized pump according to claim 5 further comprising a drive member and a tubular supporting member wherein said drive member is arranged that the center thereof is located on the axis of said output shaft of said source of driving force and said drive member is inclined in respect to said axis of said output shaft and that said drive portions of said diaphragms are respectively fixed thereto at positions near the circumferential portion of said drive member, and wherein said tubular supporting member is arranged to extend from the central portion of said drive member in the direction perpendicular to said drive member, said small-sized pump being arranged that said drive member is driven by said source of driving force in such manner that the end of said tubular supporting member performs circular motion round said axis of said output shaft of said source of driving force so as to thereby make said respective pump chambers perform pumping actions.

7. A small-sized pump according to claim 6 further comprising a collar fixed to said output shaft of said source of driving force, and a drive shaft arranged that one end thereof is eccentrically fixed to said collar in the state that said drive shaft is inclined and the other end thereof is slidably fitted into said tubular supporting member, said small-sized pump being arranged that said drive member is driven through said drive shaft and said tubular supporting member by means of rotation of said collar to be given by the driving force from said source of driving force.

8. A diaphragm pump according to claim 1 wherein said cup-like diaphragms have bottom portions and wherein said drive portions are made integral with the bottom portions of said cup-like diaphragms to form pistons.

9. A diaphragm pump in accordance with claim 8 further comprising a drive member and a tubular supporting member wherein said drive member is arranged that the center thereof is located on the axis of said output shaft of said source of driving force and said drive member is inclined in respect to said axis of said output shaft and that said drive portions of said diaphragms are respectively fixed thereto at positions near the circumferential portion of said drive member, and wherein said tubular supporting member is arranged to extend from the central portion of said drive member in the direction perpendicular to said drive member, said small-size pump being arranged that said drive member is driven by said source of driving force in such manner that the end of said tubular supporting member performs circular motion round said axis of said output shaft of said source of driving force so as to thereby make said respective pump chambers perform pumping actions.

10. A diaphragm pump according to claim 8 wherein said first check valves have a tubular form and are arranged in contact with the inside wall surfaces of said common valve chamber to cover said communicating portions.

11. A diaphragm pump according to claim 10 wherein said diaphragms are made integral with said first check valves.

12. A diaphragm pump according to claim 13 wherein an integral diaphragm body is provided in such state that said integral diaphragm body has a substantially disk-like shape and is arranged that a plural number of cup-type diaphragms formed integrally therewith an extending downward are respectively provided round the central portion of said integral diaphragm body and that a tubular valve body formed integrally therewith and extending upward is provided at the central portion of said integral diaphragm body, said integral diaphragm body being arranged that said cup-type diaphragms are respectively inserted to said cylinder-like portions of said casing and that said tubular valve body is inserted to said common valve chamber so that said tubular valve body covers said communicating portions.

13. A diaphragm pump in accordance with claim 11 further comprising a drive member and a tubular supporting member wherein said drive member is arranged that the center thereof is located on the axis of said output shaft of said source of driving force and said drive member is inclined in respect to said axis of said output shaft and that said drive portions of said diaphragms are respectively fixed thereto at positions near the circumferential portion of said drive member, and wherein said tubular supporting member is arranged to extend from the central portion of said drive member in the direction perpendicular to said drive member, said small-size pump being arranged that said drive member is driven by said source of driving force in such a manner that the end of said tubular supporting member performs circular motion round said axis of said output shaft of said source of driving force so as to thereby make said respective pump chambers perform pumping actions.

14. A diaphragm pump in accordance with claim 11 wherein an integral diaphragm body is provided in such state that said integral diaphragm body has a substantially disk-like shape and is arranged that a plural number of cup-type diaphragms formed integrally therewith and extending downward are respectively provided round the central portion of said integral diaphragm body and that a tubular valve body formed integrally therewith and extending upward is provided at the central portion of said integral diaphragm body, said integral diaphragm body being arranged that said cup-type diaphragms are respectively inserted to said cylinder-like portions of said casing and that said tubular valve body is inserted to said common valve chamber so that said tubular valve body covers said communicating portions.

* * * * *